Figure 1:
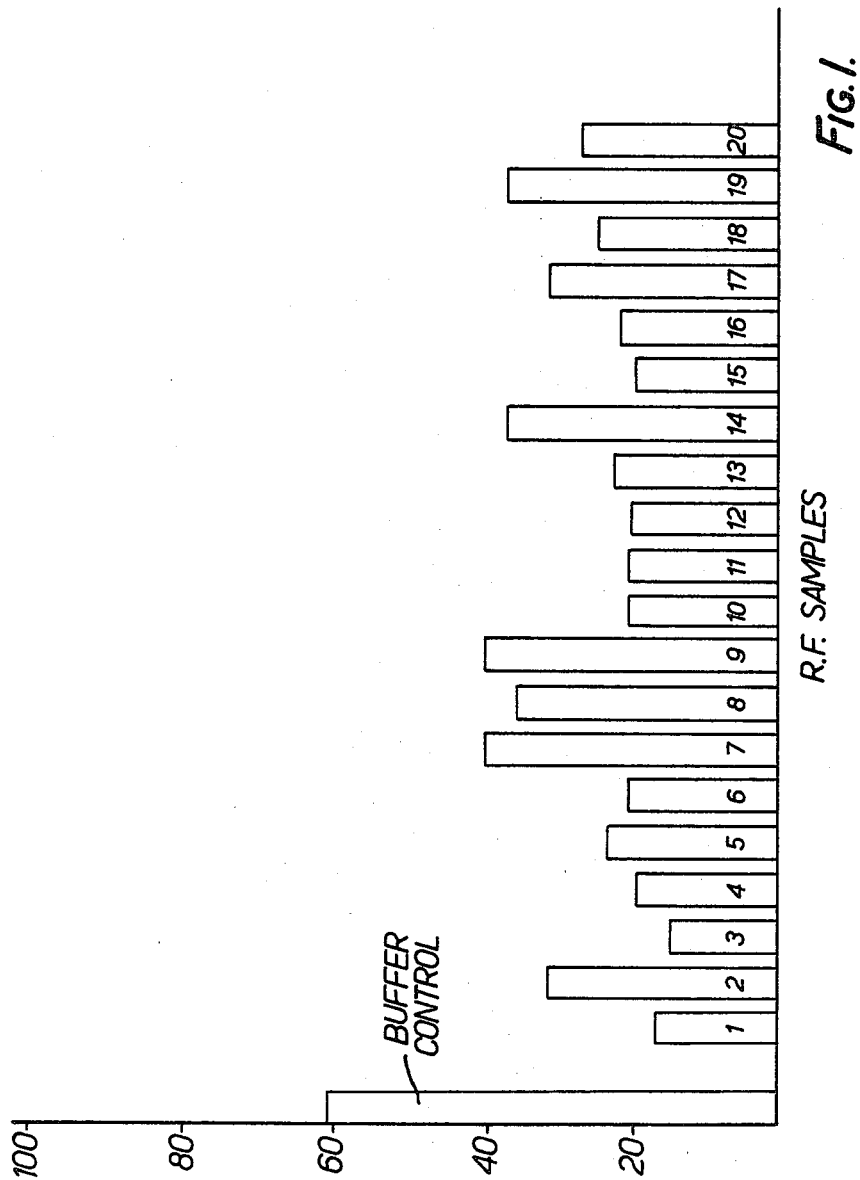

United States Patent [19]

de Steenwinkel et al.

[11] 4,362,531

[45] Dec. 7, 1982

[54] AGGLUTINATION IMMUNOASSAYS CARRIED OUT WITH AGENT TO REDUCE NON-SPECIFIC INTERFERENCES

[75] Inventors: Floris de Steenwinkel, Brussels; Daniel Collet-Cassart, Wavre; Pierre L. Masson, Brussels, all of Belgium

[73] Assignee: Technicon Instruments Corporation, Tarrytown, N.Y.

[21] Appl. No.: 254,037

[22] Filed: Apr. 14, 1981

[30] Foreign Application Priority Data

Apr. 15, 1980 [GB] United Kingdom ............... 8012428

[51] Int. Cl.³ .................... G01N 33/54; G01N 33/78
[52] U.S. Cl. .................... 23/230 B; 23/915; 252/408; 424/1; 424/12
[58] Field of Search ............ 23/230 B; 424/12; 252/408

[56] References Cited

U.S. PATENT DOCUMENTS

| | | | |
|---|---|---|---|
| 3,791,932 | 2/1974 | Schuurs | 424/12 X |
| 4,200,436 | 4/1980 | Mochido | 23/230 B |
| 4,292,038 | 9/1981 | Kondo | 424/12 X |
| 4,298,593 | 11/1981 | Ling | 424/12 X |
| 4,299,815 | 11/1981 | Hansen | 424/12 X |
| 4,305,925 | 12/1981 | Kapmeyer | 424/12 |

OTHER PUBLICATIONS

H. L. Vader et al., Clinica Chimica Acta, 80, 361–372, (1977).
Chemical Abstracts, 90:20740c, (1979).

Primary Examiner—Sidney Marantz
Attorney, Agent, or Firm—S. P. Tedesco; Charles J. Herron

[57] ABSTRACT

In particle agglutination immunoassays for an analyte (e.g. an antigen or antibody) in a liquid sample (e.g. human serum), interferences arise due to non-specific protein-protein interactions and the like. These interferences are reduced or overcome by including in the assay mixture a chaotropic or chaotropic-like agent, in a carefully controlled amount. Such agents include guanidine, guanidinium hydrochloride or thiocyanate, sodium or ammonium thiocyanate, and urea, sodium chloride and ethylenediamine tetraacetic acid.

19 Claims, 4 Drawing Figures

AGGLUTINATION IMMUNOASSAYS CARRIED OUT WITH AGENT TO REDUCE NON-SPECIFIC INTERFERENCES

This invention relates to a method of immunoassay, more particularly to a method of immunoassay involving agglutination of finely divided particles.

Immunoassays involving the agglutination of finely divided particles have been known for some time. In such assays, a liquid sample containing the analyte under assay is mixed with finely divided particles bearing a reagent (normally present as a coating thereon), and the particles agglutinate to an extent dependent on the presence and/or amount of analyte in the sample. Thereby the presence and/or amount of the analyte can be determined. There are various ways in which such assays can be effected in practice. In one well known procedure for the assay of an antigen (such as α-fetoprotein, the liquid sample is mixed with a known amount of latex particles (normally of polystyrene) which carry an antibody to the antigen. The antibody and antigen bind to form complexes, thus agglutinating the particles to an extent in proportion (but not usually direct proportion) to the amount of antigen present. The extent of agglutination may then be measured, preferably by selectively counting the unagglutinated particles.

One particular use of agglutination immunoassays is in the assay of human body fluids, such as serum for example. It has been found, however, that such fluids commonly contain, in addition to the particular analyte under assay, other materials which either cause or inhibit agglutination and so interfere in the assay, causing errors in the quantitative results. Intereference of this type cannot properly be offset by comparing the assay result with the result of a similar assay made on blank serum (viz. serum not containing the analyte in question), since the blank serum may well not be truly representative of the particular patient's serum containing the analyte under assay.

We have previously found that a major factor in causing interference in latex agglutination assays has been the presence in the liquid under assay of C1q (a component of complement) and/or rheumatoid factor (RF). These substances are endogenous to human serum. Their effect can be overcome either by removing or inactivating them, or more preferably, by using in the assay the F(ab')$_2$ fragments of the immunoglobulin antibody (in the absence of the F(c) fragments and of the whole immunoglobulin). Such a procedure is described and claimed in our U.S. patent application Ser. No. 5,261, abandoned to which reference should be made for further details.

We have further found, however, that even when the major interference from C1q and RF is avoided, there still remains some minor interference from other factors. Whilst this is usually not so serious a problem as to vitiate the assay, it does reduce the sensitivity and accuracy and, as such is clearly undesirable. We have made a variety of investigations to try to establish the cause, and remove the effect, of this interference, and we have now found a way in which it may be overcome.

In particle agglutination assay, the commonest and most widely used particles are the so-called latex particles which consist normally of a synthetic polymeric material such as polystyrene. Other types of particle, such as various clays, can be used but are not so widely applicable. A reagent is attached to the particles, the reagent being a substance which takes part in the assay reaction. Because, in most cases, the nature of the particulate material itself is such that it could, if exposed to the assay reaction mixture, enter into reaction therewith, the particulate material is conventionally masked by providing a protective coating over its surface. In cases where the reagent is itself a material which can form such a coating, e.g. an immunoglobulin then a reagent coating may be applied to protect the underlying particle core. Alternatively, and in other cases where the reagent cannot form a protective coating, e.g. where the reagent is an antigen or hapten, an inert coating is applied to the particles to cover the core. For various reasons, the most common such inert coating material is a protein, such as bovine serum albumin. The reagent may be attached to the core or to the coating. Thus, in particle agglutination assays, the particles commonly have a protein coating which is either inert to the immunospecific reaction of the assay, or constitutes a reagent in that reaction.

Whilst the provision of protein coatings on particles is commonly practised and accepted, we have now found that it contributes to the minor interference effects mentioned above. Furthermore, we have found that these minor interference effects are due in some measure to non-specific protein-protein interactions in the assay mixture. It is noteworthy that whilst such interactions quite possibly occur to some small degree in other immunoassay reaction mixtures, e.g. radioimmunoassay or fluoroimmunoassay procedures, they are probably much more significant in agglutination assays simply because it has been the common practice to use protein coatings on the particles. Thus, the deliberate practice of using protein coatings has increased the chances of protein-protein interference effects.

Having as a result of extensive investigations determined a cause of the minor interferences, we have further found that they may be eliminated or at least very substantially reduced, by including in the assay mixture controlled quantities of so-called chaotropic agents.

Chaotropic agents are known per se and have a number of properties, among which is that of breaking or weakening non-covalent bonds such as hydrogen, electrostatic and hydrophobic bonds in principle, therefore, they are suited to the purposes of the present invention in that they can reduce weak protein-protein interactions, i.e. dissociate electrostatic and hydrogen bonds. However, it has been shown (e.g. in Clinica Chimica Acta, 80 (1977), 361–372) that they also have the effect of weakening the bonding in antibody:antigen complexes. Since most agglutination immunoassays are based on antibody:antigen complex formation, it is surprising that it is possible deliberately to include chaotropic agents without any significant adverse effect. However, we have found that this is possible with, at the same time, the substantial advantage of overcoming or reducing minor interferences.

According to the present invention, there is provided a method of immunoassay for an analyte in a liquid sample, which comprises forming a mixture of the liquid sample with finely divided particles comprising a protein and a reagent, whereby specific agglutination of the particles occurs to an extent dependent on the amount of analyte present, and determining the said extent and thereby the amount of analyte present, wherein the mixture also includes one or more chaotropic or chaotropic-like agents to reduce non-specific protein interaction interferences, the amounts of said agent(s) being sufficient to reduce the effect on agglutination of said interferences.

The invention further includes a method of immunoassay for an analyte in a liquid sample, which comprises forming a mixture of the liquid sample with finely divided particles comprising a protein and a reagent, whereby specific agglutination of the particles occurs to an extent dependent on the amount of analyte present, and determining said extent and thereby the amount of analyte present, wherein (a) as a preliminary step, solutions of the same analyte as is under assay are mixed with varying amounts of a chaotropic or chaotropic-like agent and said particles, and the solutions assayed to determine the optimum range of chaotropic agent to reduce non-specific protein interaction interferences whilst retaining the desired immunospecific reaction upon which the assay is based; and then (b) assaying the analyte in said liquid sample in the presence of said chaotropic agent in an amount within said range.

As previously stated, chaotropic agents at high concentrations can affect the bonds formed between antigens and antibodies, e.g. by denaturing and proteins. It is important, therefore, in the method of the invention to keep the amount of chaotropic agent below a level at which it will seriously interfere with the desired antibody-antigen immunospecific reaction. The maximum amount of chaotropic reagent which may be present in any particular immunoassay mixture will depend on the assay in question and on the nature of the chaotropic agent itself, but it can be determined in each case by routine trial and experiment. In most cases we have found that amounts of chaotropic agent from about 0.5 up to about 2 molar are satisfactory, but the precise optimum should be checked for individual cases since it does vary.

Among the commonest chaotropic agents are guanidine, guanidinium hydrochloride or thiocyanate, sodium and ammonium thiocyanates, and urea. These are preferred for use in the assays of the invention, but other chaotropic agents such as various detergents may also be used.

It is also possible according to the present invention to use "chaotropic-like agents" by which we mean substances which would not normally be considered to be true chaotropic agents but which, nevertheless, have the property of reducing the effect of interferants in agglutination immunoassays. Examples of such "chaotropic-like agents" which we have found are sodium chloride, ethylenediamine tetra-acetic acid (EDTA), lithium nitrate, lithium chlorate, lithium isocyanate, lithium bromide, sodium bromide, potassium bromide, potassium thiocyanate, calcium chloride, lithium chloride or lithium iodide. Salts such as sodium chloride of relatively low solubility are preferably used in amounts of from about 30% to 100% of saturation. More soluble salts are used in amounts from 0.5 M to 2 M or more. EDTA is used at a concentration of from about 10 to 30 millimolar, e.g. about 20 millimolar. These substances, when used at appropriate strengths in agglutination immunoassays, have the effect of reducing interference from serum proteins. This effect seems in general to be related to an increase in the ionic strength of the serum.

As is well known, immunoassays on human sera are often effected in saline at physiological salt concentration (which is 0.9% by weight). One reason for this is to prevent precipitation of proteins present in the serum. However, at such low concentrations, sodium chloride is not a chaotropic-like agent and its use in this manner does not form part of the present invention. In order to exert a chaotropic effect, the concentration of sodium chloride has to be greater than 0.9%, e.g. 30 to 100% saturated. Similarly other substances which, at relatively high concentrations will exert a chaotropic effect, have been used in the past in particle agglutination immunoassays but only at low concentrations where they have negligible chaotropic activity. Examples of such substances are certain buffers. The use of such substances in low concentrations at which they exert little or no chaotropic activity forms no part of the present invention. It has not previously been realised in the art that the use of such substances, at higher concentrations, could have the highly advantageous effect of reducing non-specific interferences in particle agglutination assays.

As stated previously, the amount of chaotropic or chaotropic-like agent used in the method of the present invention has to be controlled carefully to achieve optimum results. In particular, a balance has to be achieved between too little agent (resulting in negligible avoidance of interference) and too much agent (resulting in a reduction in the specific agglutination reaction). In order to achieve the maximum reduction in non-specific interference whilst still retaining the specific agglutination reaction, we prefer to include in the assay mixture a macromolecular substance which enhances the specific agglutination. Examples of such substances include dextran and polyethylene glycol.

In the agglutination assays of the invention, the finely divided solid particles bear at least one reagent, the protein coating on the particles may itself constitute the reagent. Alternatively, the protein coating may be inert in the assay, and the reagent (bound to the particle core or to the protein coating) alone take part in the assay reactions. In the presence of the analyte, agglutination of the particles occurs to an extent dependent on the amount of analyte present. The extent of agglutination may be generally proportional, or inversely proportional, to the amount of analyte as will be more fully explained hereinafter. The analyte may be either an antigen (by which term we include haptens and other substances (such as drugs) which can be bound by antibodies and similar binding proteins), or an antibody (by which term we include both true antibodies and other similar binding proteins which are not strictly antibodies).

In its simplest and best known form, an agglutination immunoassay involves mixing finely divided particles bearing either an antibody or an antigen, with the sample liquid containing the analyte which is either an antigen or antibody, respectively. The analyte causes particles to agglutinate by simultaneously binding to two or more particles. The extent of agglutination then provides a meausre of the amount of analyte present. This procedure is well known.

In another procedure, described and claimed in our copending U.S. patent application Ser. No. 857,476, now U.S. Pat. No. 4,184,849 two different microcopic or submicroscopic particular reagents are used which mutually agglutinate when incubated together. The analyte inhibits such agglutination, so that in this case the amount of agglutination is inversely proportional to the amount of analyte in the sample. This procedure is particularly useful for assaying haptens. A variation of this procedure is described in our copending U.S. patent applicaton Ser. No. 06/124,849, now U.S. Pat. No. 4,279,617 where the first of the two particulate reagents binds with the analyte to form a particle:analyte complex, and the second particulate reagent agglutinates with the particle:analyte complex. This procedure is especially useful for assaying small quantities of analyte.

Reference should be made to the copending applications for further details.

In all the above cases, the amount of agglutination is preferably measured by selectively counting the unagglutinated particles, and the amount of analyte present determined thereby using standard curves (or other standard results). This technique is well-known and will not be further described herein.

The above methods of agglutination assay are given, by way of example only, of procedures which may be used in the method of the invention. Other agglutination assay procedures will be known to those skilled in the art and may also be used in the method of the invention.

In our copending U.S. patent application No. 5,261, we have described and claimed immunoassays in which there is used, in place of an antibody, the F(ab')$_2$ fragment thereof. This technique, which reduces interference by endogenous RF and C1q in assays of human serum, can be used in the method of the present invention. Thus, in the assay of an antigen analyte, the particles will bear F(ab')$_2$ fragments in place of whole antibody. Reference should be made to our copending application No. 5,261, for further details.

The method of the present invention may be effected on a manual discrete basis or in an automated continuous flow manner, as described in our copending applications referred to above.

In order that the present invention may be more fully understood, the following Examples and comparative results are given by way of illustration only. The symbol "$\mu$" means "micron".

EXAMPLE 1

Assay of horse spleen ferritin (HSF) in human serum

Polystyrene particles (diameter 0.8$\mu$) were coated with rabbit anti-HSF IgG (by aminating the polystyrene followed by diazotization by standard techniques). The particles were then incubated in various samples of serum, with and without added HSF, and with and without a chaotropic agent. The agglutination of the particles was measured after incubation at 37° C. for 30 minutes, by selectively counting the non-agglutinated particles using a Technicon Autocounter. Agglutination was expressed as the decrease in the height of the peak representing the residual non-agglutinated particles.

(a) Sera from 26 patients suffereing various diseases were tested for their agglutinating activity on the latex particles. No HSF was added to any of the sera, so that any agglutination observed was non-specific, i.e. it was not due to the immunospecific reaction between the anti-HSF IgG on the particles and free HSF in the sera. Various amounts of two chaotropic reagents were included in some of the sera. The results are shown in Table 1.

TABLE 1

| Chaotropic agent | Concentration | Coefficient of variation of peak heights |
|---|---|---|
| Guanidinium-HCl | 0 | 14.3% |
| | 0.5M | 18.6% |
| | 1M | 3.4% |
| | 2M | 2.4% |
| Na-thiocyanate | 0 | 15.9% |
| | 0.5M | 13.8% |
| | 1M | 4.3% |
| | 2M | 2.7% |

As can be seen from Table 1, the peak height with zero or little chaotropic agent, varied significantly from one serum to another, indicating the frequent occurrence of non-specific agglutination. In the presence, however, of 1 M and 2 M amounts of the two chaotropic reagents, this non-specific agglutination was very substantially reduced and the overall peak heights were very close to those observed with the particle suspension alone (i.e. without serum).

(b) The procedure of part (a) above was repeated on the sera from 20 patients but using a Billen's sampler for incubation (as opposed to the external incubation in (a)), and using latex coated with the F(ab')$_2$ fragments of rabbit anti-HSF IgG antibodies. The results are shown in Table 2.

TABLE 2

| Chaotropic agent | Concentration | Coefficient of variation of peak heights |
|---|---|---|
| Guanidinium-HCl | 0 | 12.4% |
| | 1M | 8.4% |
| Na-thiocyanate | 1M | 5.9% |
| | 1.5M | 3.4% |
| Guanidinium-thiocyanate | 0.5M | 2.5% |

The results show that, relative to Table 1, there is an overall reduction in non-specific agglutination resulting from the use of the F(ab')$_2$ fragments, but that the variation between samples was still significant. This variation is reduced substantially by the chaotropic agents, although the amounts necessary vary from one agent to another. In this particular case, guanidinium thiocyanate was the most effective. At 0.5 M concentration, the variation in peak height was very small, and the peak heights were very close to those for the particle suspension alone (without serum).

(c) HSF was added to sera from 20 patients in amounts to achieve the same concentration of HSF in each serum. Two batches of sera were thus prepared, containing respectively 5 and 100 ng HSF/ml. The amounts of HSF in each sample were then assayed by the agglutination technique described above, with and without the addition of various amounts of chaotropic agents, and the results are shown in Table 3.

TABLE 3

| Chaotropic agent | Concentration | Coefficient of variation of peak heights |
|---|---|---|
| None | | 9% for 5 ng HSF/ml |
| | | 7.7% for 100 ng/ml |
| Guanidinium-HCl | 1M | 4.3% for 5 ng/ml |
| | | 9.3% for 100 ng/ml |
| | 1.5M | 3.4% for 5 ng/ml |
| | | 8.4% for 100 ng/ml |
| Na-thiocyanate | 1M | 2.7% for 5 ng/ml |
| | | 4% for 100 ng/ml |
| | 2M | 2.4% for 5 ng/ml |
| | | 3.9% for 100 ng/ml |

The particles used had the F(ab')$_2$ fragments of rabbit anti-HSF IgG antibodies bound thereto (by the carbodiimide method). As can be seen, the main improvement occurred using sodium thiocyanate as chaotropic agent, although some improvement was also obtained with guanidinium hydrochloride. In the absence of any chaotropic agents, the variation in peak height was significant.

EXAMPLE 2

Assay of digoxin in human serum

Digoxin is a hapten which cannot satisfactorily be assayed by the direct agglutination method used in Example 1 for HSF. We therefore used the so-called mixed agglutination technique described in our aforesaid U.K. patent application No. 51740/76 now issued in the United States as U.S. Pat. No. 4,184,849. In this method, two different particulate reagents are used. The first is small particles (0.2μ) coated with antibody to the digoxin. The second is larger particles (0.8μ) coated with digoxin. When the two particulate reagents are mixed, they will mutually agglutinate. In the presence of free digoxin, however, the agglutination is inhibited by the "free" digoxin becoming bound to the small antibody-coated particles.

In such mixed agglutination procedures, serum proteins can interfere in the assay by non-specific interactions with either the small or large latex, or both, resulting in a higher or lower agglutination.

The effect of chaotropic reagents in this procedure was tested as follows.

(a) Sera from up to 25 patients were incubated with (large) latex (0.8μ). The latex was a carboxylated latex to which a conjugate of bovine serum albumin (BSA) and digoxin had been coupled by the carbodiimide method. One volume (25 μl) of a 0.05%(w/v) suspension of this latex was incubated at 25° C. for 15 minutes under continuous shaking, with one volume of five-fold diluted serum. The diluent for the serum was 0.1 M lysine—NaOH buffer (pH 9.2) containing 0.15 M NaCl, 50 mM EDTA (ethylene diamine tetracetic acid) and various concentrations of chaotropic agent (Table 4). The results are shown in part (a) of Table 4.

It can be seen that in the absence of, or at low concentrations of, chaotropic agent significant agglutination occurred in some sera. At higher concentrations of chaotropic agent, this was very substantially reduced.

(b) The procedure of part (a) was repeated except that small particles (0.2μ) coupled to anti-digoxin antibody, were also included in the mixture. Again, in the absence of chaotropic agents, or at low concentrations thereof, there was a signficant variations in peak heights because of non-specific interference from serum proteins. This was reduced with increasing amounts of chaotropic agent.

(c) The procedure of part (b) was repeated, except that digoxin (1 μg/ml) was included in each of the sera. Again, there was a very substantial variation in peak heights in the absence of chaotropic agents. However, with increasing amounts of such agents, the variation was markedly reduced to a level (about 5%) close to that of the variations in the counter itself.

Similar tests have been made using urea as the chaotropic agent, and whilst it has shown useful effects, it has not been as efficient in the above instances as guanidinium hydrochloride or sodium thiocyanate.

TABLE 4

| Chaotropic agent | Concentration | Coefficient of variation of peak heights | |
|---|---|---|---|
| (a) Digoxin-latex alone | | | |
| Guanidinium-HCl | 0 | 26% | |
| | 0.5M | 18% | on 25 samples |
| | 1M | 4% | |
| | 4M | 2.9% | |
| Na-thiocyanate | 0 | 14.5% | |
| | 0.4M | 10.1% | on 10 samples |
| | 0.8M | 9.7% | |
| | 1.6M | 5.5% | |
| Na-thiocyanate | 0 | 15.9% | |
| | 0.5M | 13.8% | on 25 samples |
| | 1M | 4.3% | |
| | 2M | 2.7% | |
| (b) Digoxin-latex (0.8 μ) + antibody-coated latex (0.2 μ) | | | |
| Guanidinium-HCl | 0 | 17.2% | |
| | 0.4M | 18.1% | on 10 samples |
| | 0.8M | 18.7% | |
| | 1.6M | 10.1% | |
| Na-thiocyanate | 0 | 14.5% | |
| | 0.4M | 10.1% | on 10 samples |
| | 0.8M | 9.7% | |
| | 1.6M | 5.5% | |
| (c) Digoxin-latex (0.8 μ) + antibody-coated latex (0.2 μ) + digoxin (1 ng/ml) | | | |
| Guanidinium-HCl | 0 | 13.3% | |
| | 0.4M | 7.2% | on 10 samples |
| | 0.8M | 11% | |
| | 1.6M | 5.2% | |
| Na-thiocyanate | 0 | 12.9% | |
| | 0.4M | 6.5% | on 10 samples |
| | 0.8M | 6.4% | |
| | 1.6M | 5.3% | |

EXAMPLE 3

Use of solutions of EDTA and NaCl in method of invention

As stated previously, there are "chaotropic-like agents" which reduce the effect of serum proteins on non-specific agglutination. Two such agents are EDTA and sodium chloride. To demonstrate this effect, an assay for serum ferritin was made in which the serum (1 part) was diluted with 9 parts of an aqueous mixture comprising 9 parts of normal rabbit serum and 1 part bovine serum albumin. 30 μl of this mixture was then mixed with 30 μl of a 10% latex suspension and 30 μl of various chaotropic solutions as shown in Table 5. As indicated in the table, in one series of tests the latex had 500 μg F(ab')$_2$ fragments per 50 μl latex, and in the other case the loading was only 90 μg F(ab')$_2$ fragments per 30 μl latex. (The fragments were derived from anti-ferritin antibodies.)

The results are shown in Table 5.

TABLE 5

| CHAOTROPIC Solution | Precision of Assay S.D. | C.V. % | Mean Value $\bar{x}$ ng/ml | Number of Samples n | Latex (Lx) |
|---|---|---|---|---|---|
| PEG (6%) in 50 mM EDTA | 9.6 | 10.8 | 88.9 | 40 | 500 μg F(ab')$_2$ Fragments per 50 μl Lx. |
| 50% sat.NaCl + PEG (6%) in 50 mM EDTA | 0.76 | 0.84 | 89.6 | 40 | |
| 3M NH$_4$SCN-PEG (6%) 50 mM EDTA | 2.3 | 2.4 | 94.1 | 40 | 90 μg F(ab')$_2$ Fragments per 30 μl Lx. |
| NaCl 50% saturated - 50 mM EDTA | 3.0 | 3.3 | 91 | 40 | 90 μg F(ab')$_2$ Fragments per 30 μl Lx. |
| NaCl 100% saturated - 50 mM EDTA | 2.6 | 2.9 | 89.8 | 40 | 90 μg F(ab')$_2$ Fragments per 30 μl Lx. |

PEG = polyethylene glycol
SD =
CV = coefficient of variation

EXAMPLE 4

Figure 2:
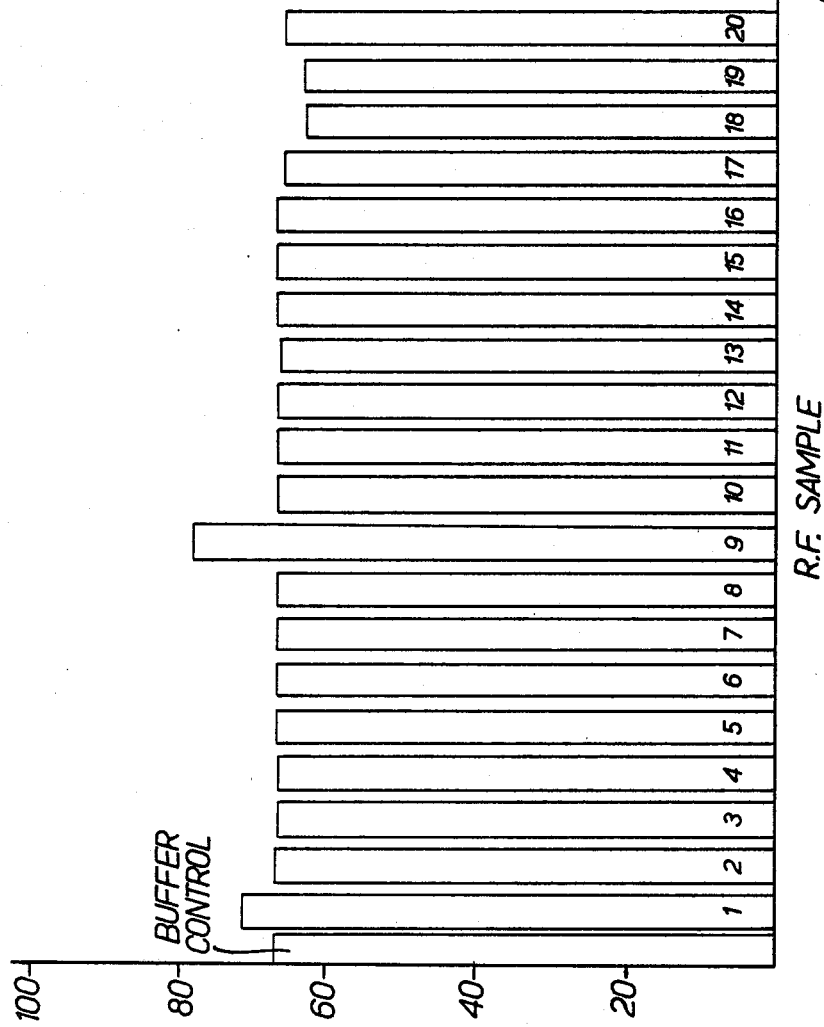

To demonstrate the effect of guanidine in reducing serum interference, samples containing thyroxine (T4) were assayed both by latex agglutination and by radioimmunoassay, in the presence of and in the absence of guanidine. The samples contained RF. The latex agglutination results are shown in FIGS. 1 and 2. FIG. 1 shows the spontaneous (i.e. in the absence of any antisera) latex agglutination results in the absence of guanidine. It can be seen that the peak heights vary considerably, whereas in FIG. 2, which shows the results when guanidine is present, there is very little variation in peak height and hence little spontaneous agglutination.

Figure 3:
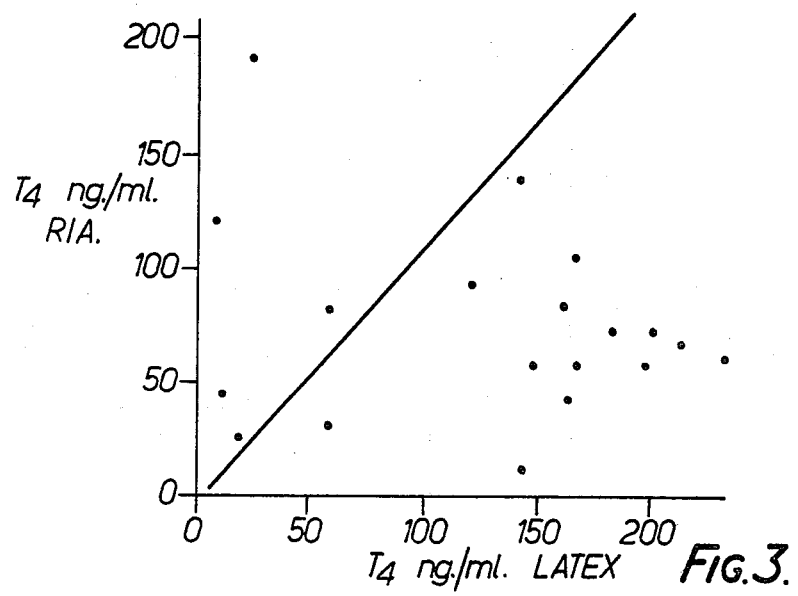
Figure 4:
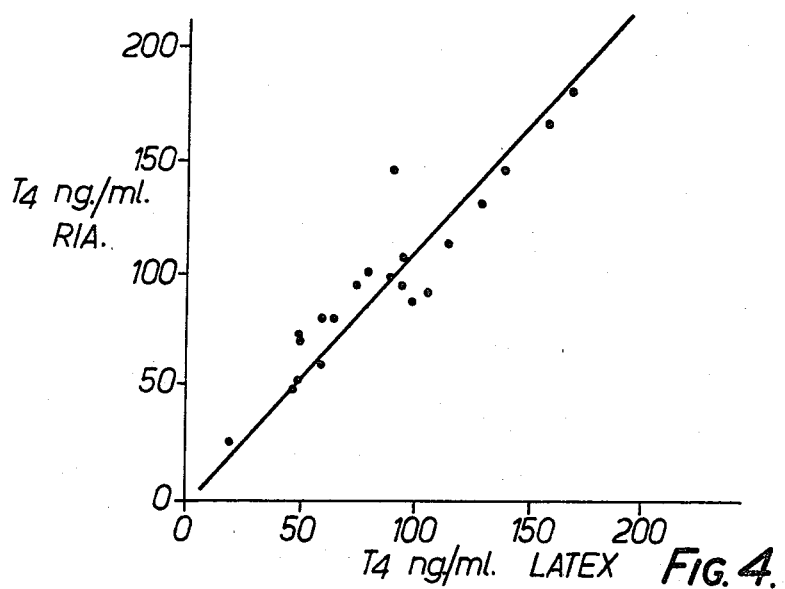

FIGS. 3 and 4 show the correlation between the latex agglutination assays and the radioimmunoassays of the same samples, without guanidine (FIG. 3) and with guanidine (FIG. 4).

The amount of guaninidine hydrochloride present in the assay mixtures was 1.28 M, and Veronal buffer (pH 9.1) was used with 0.075 M EDTA.

We claim:

1. A method of immunoassay for an analyte in a liquid sample, which comprises forming a mixture of the liquid sample with finely divided particles comprising a protein and a reagent, whereby specific agglutination or the particles occurs to an extent dependent on the amount of analyte present, and determining said extent and thereby the amount of analyte present, wherein the mixture also includes one or more agents to reduce non-specific protein interaction interferences, the amount of said agent(s) being sufficient to reduce the effect on agglutination of said interferences, wherein said agents comprise at least one compound selected from the group consisting of guanidinium hydrochloride, guanidinium thiocyanate, sodium thiocyanate, ammonium thiocyanate, sodium chloride, ethylene diamine tetraacetic acid, lithium nitrate, lithium chlorate, lithium isocyanate, lithium bromide, sodium bromide, potassium bromide, potassium thiocyanate, calcium chloride, lithium chloride and lithium iodide.

2. A method according to claim 1, wherein the agent is selected from the group consisting of sodium chloride, ethylene diamine tetra-acetic acid, lithium nitrate, lithium chlorate, lithium isocyanate, lithium bromide, sodium bromide, potassium bromide, potassium thiocyanate, calcium chloride, lithium chloride and lithium iodide.

3. A method according to claim 1, wherein the mixture also contains a macromolecular substance to enhance the specific agglutination reaction.

4. A method according to claim 1, wherein the analyte is selected from antigens and haptens, and wherein the mixture also contains the F(ab')$_2$ fragments of an immunoglobulin specific to said analyte, but is free from the whole immunoglobulin and F(c) fragments thereof.

5. A method according to claim 1, wherein the mixture contains two different particles each comprising a protein and a reagent, the particles differing in respect of the reagent.

6. A method according to claim 1, wherein said protein of which the particles are comprised also constitutes said reagent.

7. A method according to claim 1, wherein the agent is selected from guanidinium hydrochloride, guanidinium thiocyanate, sodium thiocyanate and ammonium thiocyanate.

8. A method according to claim 7, wherein the agent is present in the mixture in the amount from 0.5 M to 2 M.

9. A method according to claim 1, wherein the mixture contains two different particles each comprising a protein and a reagent, the particles differing in respect of their size.

10. A method according to claim 9, wherein said protein of which each particle is comprised also constitutes said reagent of that particle.

11. A method according to claim 1, wherein the said extent of agglutination is determined by counting unagglutinated particles.

12. A method according to claim 11, wherein the agent is selected from the group consisting of guanidinium hydrochloride, guanidinium thiocyanate, sodium thiocyanate, ammonium thiocyanate, and lithium nitrate, lithium chlorate, lithium isocyanate, lithium bromide, sodium bromide, potassium bromide, potassium thiocyanate, calcium chloride, lithium chloride and lithium iodide.

13. A method of immunoassay for an analyte in a liquid sample, which comprises forming a mixture of the liquid sample with finely divided particles comprising a protein and a reagent, whereby specific agglutination of the particles occurs to an extent dependent on the amount of analyte present, and determining the said extent and thereby the amount of analyte present, wherein (a) as a preliminary step, solutions of the same analyte as is under assay are mixed with varying amounts of an agent comprising at least one compound selected from the group consisting of guanidinium hydrochloride, guanidinium thiocyanate, sodium thiocyanate, ammonium thiocyanate, sodium chloride, ethylene diamine tetraacetic acid, lithium nitrate, lithium chlorate, lithium isocyanate, lithium bromide, sodium bromide, potassium bromide, potassium thiocyanate, calcium chloride, lithium chloride and lithium iodide and said particles, and the solutions assayed to determine the optimum range of said agent to reduce non-specific protein interaction interferences whilst retaining the desired immunospecific reaction upon which the assay is based; and then (b) assaying the analyte in said liquid sample in the presence of said agent in an amount within said range.

14. A particle agglutination specific binding assay composition for the non-specific protein interaction interference-free determination of an analyte in a liquid sample, which composition comprises:

a particle to which is bound protein and a specific binding partner for said analyte; and an agent comprising at least one compound selected from the group consisting of guanidinium hydrochloride, guanidinium thiocyanate, sodium thiocyanate, ammonium thiocyanate, sodium chloride, ethylene diamine tetraacetic acid, lithium nitrate, lithium chlorate, lithium isocyanate, lithium bromide, sodium bromide, potassium bromide, potassium thiocyanate, calcium chloride, lithium chloride and lithium iodide.

15. The particle agglutination specific binding assay composition of claim 14, wherein said agent comprises at least one compound selected from the group consisting of sodium chloride, ethylene diamine tetraacetic acid, lithium nitrate, lithium chlorate, lithium isocyanate, lithium bromide, sodium bromide, potassium bromide, potassium thiocyanate, calcium chloride, lithium chloride and lithium iodide.

16. The particle agglutination specific binding assay composition of claim 14, wherein said agent comprises at least one compound selected from the group consisting of guanidinium hydrochloride, guanidinium thiocyanate, sodium thiocyanate and ammonium thiocyanate.

17. The particle agglutination specific binding assay composition of claim 16, wherein said agent comprises sodium thiocyanate.

18. A particle agglutination specific binding assay method for the non-specific protein interference-free determination of an analyte in a liquid sample, which method comprises:

contacting said liquid sample with a composition which comprises a particle to which is bound protein and a specific binding partner for said analyte and an agent which comprises at least one compound selected from the group consisting of guanidinium hydrochloride, guanidinium thiocyanate, sodium thiocyanate, ammonium thiocyanate, sodium chloride, ethylene diamine tetraacetic acid, lithium nitrate, lithium chlorate, lithium isocyanate, lithium bromide, sodium bromide, potassium bromide, potassium thiocyanate, calcium chloride, lithium chloride and lithium iodide; and, thereafter, observing any particle agglutination which occurs.

19. The method of claim 18 wherein the step of contacting comprises contacting said liquid sample with a composition wherein said chaotropic agent includes at least one compound selected from one group consisting of guanidinium hydrochloride, guanidinium thiocyanate, sodium thiocyanate and ammonium thiocyanate.

* * * * *